United States Patent [19]
Eldor

[11] Patent Number: 5,848,996
[45] Date of Patent: Dec. 15, 1998

[54] MULTIPLE HOLE SPINAL NEEDLE

[76] Inventor: Joseph Eldor, 4 Hanayadot Street, Pisgat Zeev, Jerusalem 97536, Israel

[21] Appl. No.: 858,126

[22] Filed: May 19, 1997

Related U.S. Application Data

[63] Continuation of Ser. No. 576,015, Dec. 21, 1995, abandoned.

[30] Foreign Application Priority Data

Feb. 15, 1995 [IL] Israel ..................................... 112652

[51] Int. Cl.$^6$ ...................................... A61M 5/32

[52] U.S. Cl. ........................... 604/272; 604/164; 604/264

[58] Field of Search .................... 604/272, 274, 604/164, 280, 53, 158, 264, 273, 170

[56] References Cited

U.S. PATENT DOCUMENTS

| | | | |
|---|---|---|---|
| 564,581 | 7/1896 | Baker | 604/274 X |
| 4,411,657 | 10/1983 | Galindo | 604/274 |
| 4,737,146 | 4/1988 | Amaki et al. . | |
| 4,790,830 | 12/1988 | Hamacher | 604/274 |
| 4,838,877 | 6/1989 | Massau | 604/264 |
| 5,078,688 | 1/1992 | Lobodzinski et al. | 604/164 |
| 5,100,390 | 3/1992 | Lubeck et al. . | |
| 5,234,406 | 8/1993 | Drasner et al. . | |
| 5,254,106 | 10/1993 | Feaster | 604/272 |
| 5,449,351 | 9/1995 | Zohmann | 604/158 X |
| 5,478,328 | 12/1995 | Silverman et al. | 604/272 |

OTHER PUBLICATIONS

Greene, "Lumbar Punture and the Prevention of Post–Puncture Headache", *JAMA*, vol. 86, pp. 391–392 (1926).

Kirschner, "Versuche Zur Herstellung Einer Gurtelformigen Spinal Anaesthesia", *Arch. Klin. Chir.*, vol. 167, pp. 755–760 (1931).

Hart et al., "Pencil–point Needle in Prevention of Postspinal Headache", *JAMA*, vol. 147, pp. 657–658 (1951).

Sprotte et al., "Eine Atraumatishe Universalkanule fur Einzeitige Regionalanaesthesien", *Reg. Anaesthe.* vol. 10, pp. 104–108 (1987).

Sosis et al., An In–Vitro Evaluation of the New Shorter Orifice Sprotte Spinal Needle, *Anesth. Analg.* vol. 78, p. S410 (1994).

Lipov et al., "Does the Design of the Sprotte Spinal Needle Reduce the Force Needed to Deform the Tip?" *J. Clin. Anesth.*, vol. 6, pp. 411–413 (1994).

*Primary Examiner*—John D. Yasko
*Attorney, Agent, or Firm*—Kohn & Associates

[57] ABSTRACT

A double-hole pencil-point (DHPP) spinal needle is composed of a closed end blunt ogival or pencil point tip and two circular coaxial holes in close proximity to the tip. Anesthetic solution may be injected through the coaxial holes in a direction parallel to the long axis of the spinal fluid column which allows an even anesthetic distribution with a low dosage required. The spinal needle of the present invention allows anesthetic solution to be injected even when one of the holes is obstructed by a tissue fragment and rapid reflux of cerebral spinal fluid at twice the rate of single hole pencil point spinal needles.

22 Claims, 1 Drawing Sheet

MULTIPLE HOLE SPINAL NEEDLE

CROSS-REFERENCE OF RELATED APPLICATIONS

This is a continuation of application Ser. No. 08/576,015 filed on Dec. 21, 1995 now abandoned.

The present invention is based upon Israel Patent Application No. 112652 filed on Feb. 15, 1995, the disclosure of which is incorporated herein by reference in its entirety.

BACKGROUND OF THE INVENTION

1. Field of the Invention

The present invention relates to a device for spinal anesthesia. In particular, the present invention relates to a double-hole pencil-point (DHPP) spinal needle.

2. Discussion of the Background Information

In 1926, a needle with a round, tapering, and sharp point was described by Greene in, "Lumbar Puncture and the Prevention of Post-Puncture Headache", *JAMA*, vol. 86, pp. 391–92 (1926). This article was the result of experiments made during 1923 and of experience and observation following those experiments. The article concluded that "post-puncture headache is caused by trauma to the spinal dura sufficient to result in excessive leakage of cerebrospinal fluid to the point at which the brain is left without a water cushion". These experiments demonstrated that a greater trauma was produced by the use of a needle with a blunt cutting point than by a needle of the same caliber with a rounded, tapered and sharpened point. It was also found possible to pass a small sharp, round, tapering pointed instrument between the fibers of a spinal dural sac, suspended and filled with water, without cutting any of them. He performed 215 consecutive punctures with this needle, with a headache incidence of only two in the series.

In 1931, Kirschner, in "Versuche Zur Herstellung Einer Gurtelformigen Spinal Anaesthesia", *Arch. Klin. Chir.*, vol. 167, pp. 755–60 (1931) described a needle for spinal anesthesia. The needle described by Kirschner was formed with an opening in the shaft proximal to the beveled closed end. This needle was recommended to give more accurate control to the duration and extent of anesthesia because the needle could be manipulated to permit injection of solution in a direction parallel to the long axis of the spinal fluid column rather than against the side of the canal opposite puncture.

Hart and Whitacre (4) described a pencil-point spinal needle in "Pencil-Point Needle in Prevention of Postspinal Headache", *JAMA*, vol. 147, pp. 657–658 (1951). The pencil point spinal needle, known as the Whitacre needle, is shown in FIG. 2.

The Whitacre needle was modified by Sprotte et al., "Eine Atraumatishe Universalkanule fur Einzeitige Regionalanaesthesien", *Reg. Anaesthe.*, vol. 10, pp. 104–8 (1987). The needle has since been known as the Sprotte needle, shown in FIG. 1. In the years since the Sprotte needle was described, there has been a resurgence of spinal anesthesia in many operating rooms around the world. This resurgence has been fueled by a breakthrough in regional anesthesia called combined spinal-epidural anesthesia. The pencil-point spinal needle is an exceptional device for delivering the anesthesia. Consequently, the FDA only approves of using pencil-point spinal needle in the needle-through-needle or Eldor needle techniques for combined spinal-epidural anesthesia.

However, the long orifice 101 of a 24 gauge Sprotte spinal needle may result in failed spinal anesthetics because the length of the orifice 101 exceeds the 1 mm thickness of human lumbar dura. Accordingly, Sprotte modified his spinal needle by reducing the length of the orifice. However, Sosis et al., in "An In-Vitro Evaluation of the New Shorter Orifice Sprotte Spinal Needle", *Anesth. Analg.*, vol. 78, pg. S410 (1994) compared in-vitro the 1.8 mm long lateral orifice of the original version of the Sprotte spinal needle with the 1.0 mm long orifice of the modified Sprotte needle. Sosis et al. found that the flow of water through the needle was not reduced even after the orifice length was reduced by 44%.

Lipov et al. examined whether the window design of Sprotte pencil-point needles leads to deformation under lateral or axial loading conditions. "Does the Design of the Sprotte Spinal Needle Reduce the Force Needed to Deform the Tip?", *J. Clin. Anesth.*, vol. 6, pp.411–13 (1994) examined the 22- and 24-gauge Sprotte needles, 22- and 25-gauge Whitacre needles, and 22- and 25-gauge Quincke needles. The lateral or axial force required to bend a Sprotte needle was less than necessary for either of the Whitacre or Quincke needles of similar size. It was also noted that the tips of the Sprotte needles were most likely to bend at the needle window, while the Quincke and Whitacre needles deformed at the clamping point. Lipov et al. concluded that Sprotte needles have an inherent design weakness to lateral and axial pressure, which may result in a greater number of needle tip deformations upon insertion. As a result of this deformation, difficulty in needle withdrawal and possibility of needle tip fracture may occur.

SUMMARY OF THE INVENTION

It is an object of the present invention to provide a spinal needle that avoids the risk of needle deformation due to bending at the window, as with Sprotte needles. It is another object of the present invention to provide a spinal needle which doubles rapid cerebral spinal fluid (CSF) reflux.

According to one aspect of the present invention, a new pencil-point spinal needle is described that avoids the drawbacks of conventional Sprotte and Whitacre needles.

Accordingly, a double-hole pencil-point (DHPP) spinal needle is composed of a closed end blunt ogival, or pencil-point, tip and two circular holes opposing each other in close proximity to the tip. The area of each of the two holes is approximately one-half the area of a single Sprotte hole.

According to another aspect of the present invention, the anesthetic solution injected through the coaxial holes allows more even anesthetic distribution and less anesthetic solution dosage.

According to yet another aspect of the present invention, the DHPP spinal needle allows anesthetic solution to be injected even when one of the holes is obstructed by a tissue fragment.

Accordingly, the present invention provides a device for spinal anesthesia that includes a pencil point needle. The needle includes two coaxially disposed round holes proximal to a tip.

According to another aspect of the present invention, the two coaxially disposed round holes have the same diameter.

According to a further aspect of the present invention, an obturator, insertable within the needle, is provided for closing the coaxially disposed holes from the inside of the needle.

According to yet another aspect of the invention, the needle includes a length sufficient to linearly penetrate dura matter and enter a subarachnoid space, so that the tip and the two coaxially disposed round holes are concurrently positionable within the subarachnoid space.

According to another aspect of the present invention, the device include cerebral spinal fluid refluxing through the two coaxial holes.

According to another aspect of the invention, an anesthetic solution is included for injecting through the needle to flow outwardly through the two coaxially disposed round holes into a subarachnoid space.

Accordingly, the present invention also provides a needle for penetrating a spinal fluid column and dispensing anesthesia that includes an ogival tip with a perforating end and a hollow shaft. The shaft includes a pair of coaxially positioned apertures and the tip and shaft are coupled through the apertures.

According to another aspect of the present invention, a diameter of the apertures is between approximately 0.008 and 0.0135 inches.

According to yet another aspect of the present invention, the apertures are positioned such that a distance between the perforating end and a leading edge of the apertures is between approximately 0.025 and 0.055 inches.

According to a further aspect of the invention, an outside diameter of the needle is between approximately 0.0180 and 0.0185 inches.

According to another aspect of the invention, an inside diameter of the needle is between approximately 0.0115 and 0.0130 inches.

BRIEF DESCRIPTION OF THE DRAWINGS

The present invention is further described in the detailed description which follows, by reference to the noted plurality of drawings by way of non-limiting examples of preferred embodiments of the present invention, in which like reference numerals represent similar parts throughout the several views of the drawings, and wherein.

DETAILED DESCRIPTION OF THE PREFERRED EMBODIMENT

The particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1:
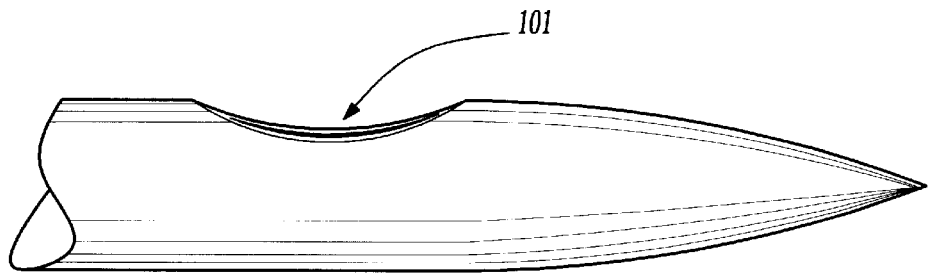
FIG. 1 shows a prior art Sprotte needle device.
Figure 2:
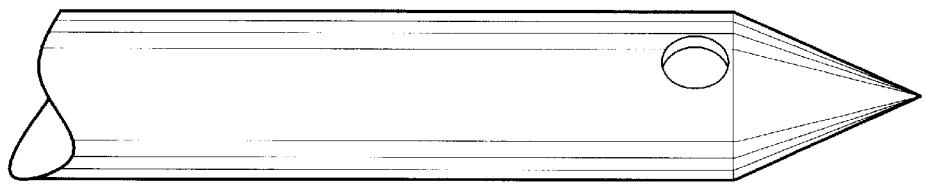
FIG. 2 shows a prior art Whitacre needle.
Figure 3:
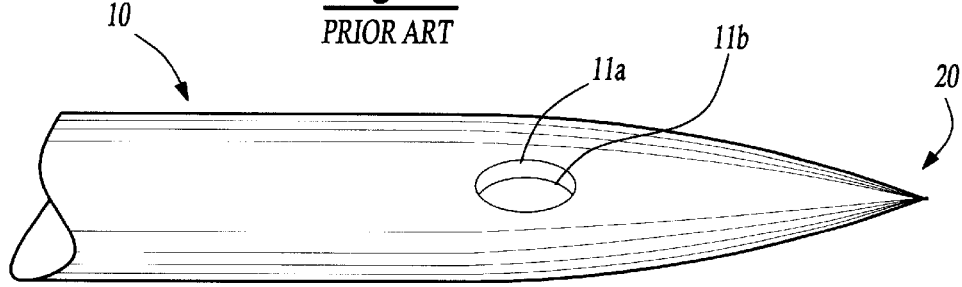
FIG. 3 shows a top view of the device according to the invention.
Figure 4:
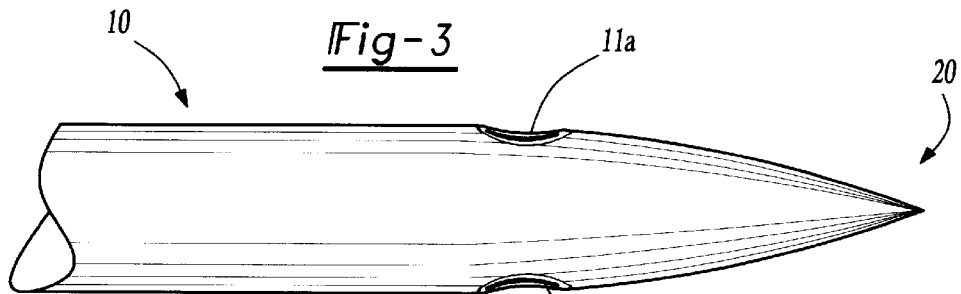
FIG. 4 shows a lateral view of the device according to the present invention.

FIGS. 3 and 4 show an insertion end of a double-hole pencil-point (DHPP) needle 10 of the present invention. The pencil point needle includes a blunt tip 20 for performing, e.g., a lumbar puncture. The needle 10 also includes two coaxially disposed holes 11a, 11b preferably of even diameter and positioned in proximity to the tip 20. Holes 11a, 11b are positioned such that anesthetic solution flowing through needle 10 is forced through the holes 11a, 11b and in opposite directions.

According to the present invention, the diameter of coaxial holes 11a, 11b within the spinal needle 10 may be between, for example, approximately 0.008 and 0.0135 in. The distance from tip 20 to hole 11a (or 11b) is intended to remain small so that the tip and coaxial holes may be positionable within the subarachnoid space together. Thus, the preferred distance between the tip 20 and a leading edge of hole 11a (or 11b) is between, for example, approximately 0.025 and 0.055 in. The outside diameter of the spinal needle 10 may be between, e.g., 0.0180 and 0.0185 in. while the inside diameter may be between, e.g., 0.0115 and 0.0130 in. While the overall length of the spinal needle may vary according to the user's needs, the length must be sufficient to enable the tip and holes to penetrate the dura matter and enter the subarachnoid space.

Figure 5:
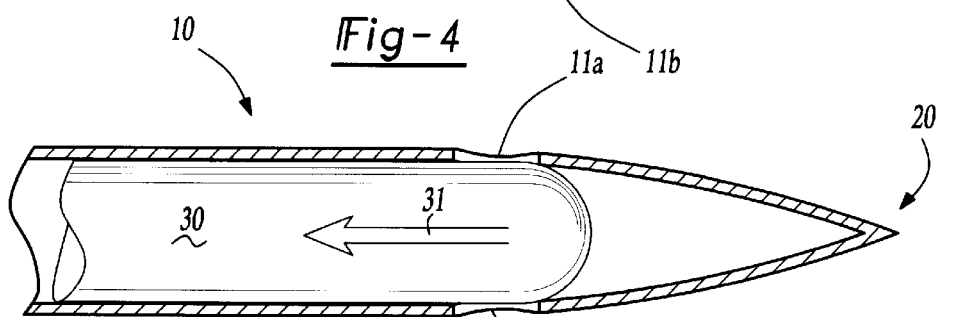
FIG. 5 shows a sectional view of the device according to the present invention and an obturator.

In use, the needle is generally positioned such that the holes 11a, 11b are to be coaxially aligned with the long axis of the spinal fluid column and designed for linear penetration of the dura matter and for entering the subarachnoid space. As shown in FIG. 5, an obturator 30 or mandrel, which may be made of conventional design and materials as known to those ordinarily skilled in the art, may be inserted within the spinal needle to cover and block holes 11a, 11b from the inside during insertion, as shown in the phantom lines. The obturator 30, positioned as shown in the phantom lines, enables the spinal needle to penetrate tissue without any tissue fragments entering the internal portion of the needle. Once the needle is properly inserted, the obturator 30 is completely removed from the needle in a left direction along arrow 31 to enable the injection of anesthesia.

The preferred embodiment of the present invention allows anesthetic to flow into the spinal fluid column through, e.g., hole 11b, even when one of the holes, e.g., 11a, is blocked or obstructed by, e.g., a tissue fragment. Further, the dual directed, i.e., unobstructed, injection of anesthetic solution into the spinal fluid column enhances the diffuse distribution while reducing the required dosage amount.

The pencil-point needle, according to the present invention, may be made of metal or similar composition, as known by those ordinarily skilled in the art. Further, the pencil-point needle may also be used in the same manner as the conventional pencil point needles described above, without suffering the noted drawbacks. The reduced hole size of the present invention avoids the risk of deformation so common in Sprotte needles. Whereas, the double hole design enables the rapid CSF reflux on the order of twice that of the single hole Whitacre needle.

It is noted that the foregoing examples have been provided merely for the purpose of explanation and are in no way to be construed as limiting of the present invention. While the invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the invention in its aspects. Although the invention has been described herein with reference to particular means, materials and embodiments, the invention is not intended to be limited to the particulars disclosed herein; rather, the invention extends to all functionally equivalent structures, methods and uses, such as are within the scope of the appended claims.

What is claimed is:

1. A needle for penetrating a spinal fluid column and dispensing anesthesia consisting of:
   a substantially conical or ogival pencil point tip including a perforating end;
   a hollow substantially cylindrical shaft, and a pair of coaxially positioned apertures disposed at a junction of said shaft and tip, and said tip and shaft being coupled through said apertures, said needle further comprising a length sufficient to linearly penetrate dura matter and enter a subarachnoid space, so that said tip and said two coaxially disposed apertures are concurrently positionable within the subarachnoid space.

2. A needle for penetrating a spinal fluid column and dispensing anesthesia consisting of
   substantially conical or ogival tip including a perforating end; and
   a hollow substantially cylindrical shaft, said shaft including a pair of coaxially positioned apertures, disposed at a junction of said shaft and tip and said tip and shaft being coupled through said apertures.

3. The needle according to claim 2, said needle comprising a length sufficient to linearly penetrate dura matter and enter a subarachnoid space, so that said tip and said two coaxially disposed apertures are concurrently positionable within the subarachnoid space.

4. The needle according to claim 3, wherein a diameter of said apertures is between approximately 0.008 and 0.0135 inches.

5. The needle according to claim 3, wherein said apertures are positioned such that a distance between said perforating end and a leading edge of said apertures is between approximately 0.025 and 0.055 inches.

6. The needle according to claim 2, wherein an outside diameter of said needle is between approximately 0.0180 and 0.0185 inches.

7. The needle according to claim 5, wherein an inside diameter of said needle is between approximately 0.0115 and 0.0130 inches.

8. The needle according to claim 2, wherein said apertures are substantially the same diameter.

9. The needle according to claim 2, said needle further comprising an obturator for covering and blocking said apertures during insertion of said needle into tissue.

10. The needle according to claim 2, further comprising an anesthetic solution for injecting through said needle to flow outwardly through said apertures.

11. The needle according to claim 3, further comprising an anesthetic solution for injecting into the subarachnoid space.

12. The needle according to claim 11, said anesthetic solution injected through said apertures.

13. The needle according to claim 12, wherein said apertures are substantially equal in diameter.

14. The needle according to claim 3, wherein said apertures are substantially equal in diameter.

15. A needle for penetrating a spinal fluid column and dispensing anesthesia consisting of:
   a substantially conical or ogival pencil point tip including a perforating end;
   a hollow substantially cylindrical shaft, and a pair of coaxially positioned apertures disposed at a junction of said shaft and tip, and said tip and shaft being coupled through said apertures.

16. The needle according to claim 15, wherein a diameter of said apertures is between approximately 0.008 and 0.0135 inches.

17. The needle according to claim 15, wherein said apertures are positioned such that a distance between said perforating end and a leading edge of said apertures is between approximately 0.025 and 0.055 inches.

18. The needle according to claim 15, wherein an outside diameter of said needle is between approximately 0.0180 and 0.0185 inches.

19. The needle according to claim 15, wherein an inside diameter of said needle is between approximately 0.0115 and 0.0130 inches.

20. A needle for penetrating a spinal fluid column and dispensing anesthesia consisting of:
   a substantially conical or ogival pencil point tip including a perforating point generally expanding out to a distal end;
   a hollow substantially cylindrical shaft portion; and
   a pair of coaxially positioned apertures disposed at a junction of said shaft and tip, extending through said shaft portion directly adjacent to said distal end of said pencil point tip.

21. The needle according to claim 20, wherein said pencil point tip is conical.

22. The needle according to claim 20, wherein said pencil point tip is ogival.

* * * * *